(12) United States Patent
Lin et al.

(10) Patent No.: US 10,089,391 B2
(45) Date of Patent: Oct. 2, 2018

(54) ONTOLOGICAL INFORMATION RETRIEVAL SYSTEM

(75) Inventors: Wilfred Wan Kei Lin, Hong Kong (CN); Allan Kang Ying Wong, Hong Kong (CN); Jackei Ho Kei Wong, Hong Kong (CN); Jewels Chun Wing Kong, Hong Kong (CN)

(73) Assignee: HERBMINERS INFORMATICS LIMITED, Hong Kong (CN)

( * ) Notice: Subject to any disclaimer, the term of this patent is extended or adjusted under 35 U.S.C. 154(b) by 65 days.

(21) Appl. No.: 13/318,849

(22) PCT Filed: Jul. 29, 2010

(86) PCT No.: PCT/IB2010/002237
§ 371 (c)(1),
(2), (4) Date: Dec. 22, 2011

(87) PCT Pub. No.: WO2011/013007
PCT Pub. Date: Feb. 3, 2011

(65) Prior Publication Data
US 2012/0124051 A1    May 17, 2012

Related U.S. Application Data

(60) Provisional application No. 61/229,545, filed on Jul. 29, 2009.

(51) Int. Cl.
*G06F 17/30* (2006.01)
*G06F 19/00* (2018.01)
*G16H 50/70* (2018.01)

(52) U.S. Cl.
CPC ...... *G06F 17/30734* (2013.01); *G06F 19/324* (2013.01); *G16H 50/70* (2018.01)

(58) Field of Classification Search
CPC .................................................. G06F 17/30734
(Continued)

(56) References Cited

U.S. PATENT DOCUMENTS

| | | | |
|---|---|---|---|
| 6,601,055 B1 * | 7/2003 | Roberts | G06F 19/345 |
| | | | 600/300 |
| 6,687,685 B1 * | 2/2004 | Sadeghi | G06F 19/3418 |
| | | | 600/300 |

(Continued)

FOREIGN PATENT DOCUMENTS

| | | |
|---|---|---|
| CN | 1645364 | 7/2005 |
| CN | 101408912 | 4/2009 |
| CN | 101441682 | 5/2009 |

*Primary Examiner* — Miranda Le
(74) *Attorney, Agent, or Firm* — Saliwanchik, Lloyd & Eisenschenk

(57) ABSTRACT

An ontological information retrieval system is provided. According to an embodiment, the subject ontological information retrieval system can be utilized for computer-aided clinical Traditional Chinese Medicine (TCM) practice. In one implementation, a graphical user interface (GUI) is provided, enabling a user to input a query with symptoms determined from a patient, and the system's parser can find instances of the symptoms in a document object model (DOM) tree of the TCM ontological information. Diagnosis based upon the symptoms can be communicated to the user through the GUI. A relevance index (RI) and/or a frequency index (FI) can be further provided for evaluating a diagnosis by comparing the symptoms determined from a patient with the expected symptoms of the diagnosed illness and returning a value based on the number of matched symptoms, or a weighted index of matched symptoms.

10 Claims, 6 Drawing Sheets

(58) Field of Classification Search
USPC .......... 707/739, 755, 999.003, 999.005, 748, 707/750, 794
See application file for complete search history.

(56) References Cited

U.S. PATENT DOCUMENTS

| | | | |
|---|---|---|---|
| 6,745,157 B1* | 6/2004 | Weiss et al. ..................... 703/2 |
| 7,149,756 B1* | 12/2006 | Schmitt et al. |
| 7,222,066 B1* | 5/2007 | Oon ................................ 704/9 |
| 7,305,389 B2* | 12/2007 | Zeng et al. ................... 707/721 |
| 7,344,496 B2* | 3/2008 | Iliff ............................... 600/300 |
| 7,444,071 B2* | 10/2008 | Chen .................... A61B 5/0059 128/922 |
| 7,493,253 B1* | 2/2009 | Ceusters ............ G06F 17/2775 704/10 |
| 7,512,576 B1* | 3/2009 | Syeda-Mahmood ................. G06F 17/30734 706/45 |
| 7,630,947 B2* | 12/2009 | Pandya ............... G06F 19/345 706/45 |
| 7,739,104 B2* | 6/2010 | Berkan et al. .................... 704/9 |
| 7,739,123 B1* | 6/2010 | Rappaport ...................... 705/2 |
| 7,899,764 B2* | 3/2011 | Martin et al. ................. 706/12 |
| 8,060,513 B2* | 11/2011 | Basco et al. ................. 707/739 |
| 8,150,857 B2* | 4/2012 | Benson ........................ 707/748 |
| 8,244,733 B2* | 8/2012 | Fortier et al. ................. 707/741 |
| 8,433,715 B1* | 4/2013 | Mirhaji ......................... 707/756 |
| 8,560,550 B2* | 10/2013 | Patterson .................... 707/741 |
| 8,781,813 B2* | 7/2014 | Cooper ................ G06F 17/275 704/9 |
| 8,888,697 B2* | 11/2014 | Bowman ............... G06F 19/322 600/300 |
| 2001/0003183 A1* | 6/2001 | Thompson ........ G06F 17/30395 |
| 2001/0039503 A1* | 11/2001 | Chan .................... G06F 19/322 705/2 |
| 2002/0165737 A1* | 11/2002 | Mahran ............................ 705/3 |
| 2003/0050803 A1* | 3/2003 | Marchosky ........... G06F 19/322 705/3 |
| 2003/0139652 A1* | 7/2003 | Kang ..................... A61B 5/00 600/300 |
| 2004/0093331 A1* | 5/2004 | Garner et al. .................... 707/3 |
| 2004/0122704 A1* | 6/2004 | Sabol .................... G06F 19/321 705/2 |
| 2004/0199332 A1* | 10/2004 | Iliff ................................ 702/19 |
| 2005/0181350 A1* | 8/2005 | Benja-Athon ........ G06F 19/363 434/367 |
| 2006/0020466 A1* | 1/2006 | Cousineau et al. ........... 704/257 |
| 2006/0036430 A1* | 2/2006 | Hu ................................ 704/10 |
| 2006/0136403 A1* | 6/2006 | Koo .............................. 707/3 |
| 2006/0183099 A1 | 8/2006 | Feely et al. |
| 2007/0005621 A1* | 1/2007 | Lesh ................. G06F 19/3487 |
| 2007/0050344 A1* | 3/2007 | Rind et al. ...................... 707/3 |
| 2008/0040150 A1* | 2/2008 | Kao ...................... G06F 19/322 705/2 |
| 2008/0077581 A1* | 3/2008 | Drayer et al. .................... 707/5 |
| 2008/0228769 A1* | 9/2008 | Lita et al. ........................ 707/6 |
| 2008/0270120 A1* | 10/2008 | Pestian et al. .................... 704/9 |
| 2009/0070103 A1* | 3/2009 | Beggelman et al. ............. 704/9 |
| 2009/0076847 A1* | 3/2009 | Gogolak ......................... 705/2 |
| 2009/0083203 A1* | 3/2009 | Cho et al. ....................... 706/21 |
| 2009/0119095 A1* | 5/2009 | Beggelman ......... G06F 17/2785 704/9 |
| 2009/0198511 A1* | 8/2009 | Boehlke .......................... 705/2 |
| 2010/0010806 A1* | 1/2010 | Bi et al. ......................... 704/10 |
| 2010/0094874 A1* | 4/2010 | Huber et al. .................. 707/740 |
| 2010/0121832 A1* | 5/2010 | Adsera Bertran ............. 707/706 |
| 2011/0004628 A1* | 1/2011 | Armstrong et al. .......... 707/778 |
| 2011/0119212 A1* | 5/2011 | De Bruin et al. .............. 706/12 |
| 2011/0184748 A1* | 7/2011 | Fierro .................... G06Q 10/00 705/2 |

* cited by examiner

| | |
|---|---|
| Severe aversion to cold | |
| Alterations in cold and heat | Head and body |
| Normal stool | Normal urination |
| Diet | Chest and abdominal |
| Sore limbs after sweating | Ears and eyes |
| Cough and little sputum | Yellowish, sticky sputum |
| Pain | Form |
|    Body parts | |
| Sleep | Complexion (pale) |
| Stuffy nose, runny nose | Chapped lips |
| Pharynx | Vomit food acidic |
| Abnormal mental state | |
| Tongue | |
|    Pink tongue | |
|    Thin, white tongue | |
| pulse | |

Figure 2

| | | |
|---|---|---|
| Internal medicine<br>- flu<br>  - wind-cold syndrome<br>    - main symptoms<br>        - severe aversion to cold<br>           • id = "1"<br>        - mild fever<br>           • id = "1"<br>        - no sweat<br>           • id = "1"<br>        - headache<br>           • id = "1"<br>        - sore limbs<br>           • id = "1"<br>        - stuffy nose, runny nose<br>           • id = "1"<br>        - sneezing<br>           • id = "1"<br>        - pharynx<br>           • id = "1"<br>        - severe cough<br>           • id = "1"<br>        - thin, pale complexion<br>           • id = "1"<br>    - related symptoms<br>        - not thirsty<br>           • id = "1"<br>        - prefer hot drinks<br>           • id = "1"<br>    - tongue surface<br>        - thin, white<br>           • id = "1"<br>    - pulse<br>        - floating<br>           • id = "1"<br>        - rapid<br>           • id = "1"<br>  - wind-heat syndrome<br>        - mild aversion to cold<br>           • id = "1"<br>        - high fever<br>           • id = "1"<br>        - sweating<br>           • id = "1"<br>        - severe headache<br>           • id = "1" | Heat in the palms | Joint pain |
| | Normal stool | Normal urination |
| | Lack of appetite | Dull chest pain |
| | Little night sweat | Ears and eyes |
| | Lung cough | Little white sticky sputum |
| | Pain | Pale complexion |
| | Chest | |
| | Sleeplessness | Dull pain |
| | Stuffy nose, sneezing | Thirsty |
| | Pharynx | Acidic food |
| | Mental state | |
| | Tongue | |
| | [image] | |
| | Thin, yellowish fur | |
| | Dry and reddish (tongue) | |
| | Little fur | |
| | Thin fur | |
| | Yellowish fur | |
| | Little fur or yellowish fur | |
| | Grey | |
| | [image] fur | |
| | Pulse | |

Figure 3

| | | |
|---|---|---|
| Internal medicine<br>  - flu<br>    - wind-cold syndrome<br>      - main symptoms<br>         - severe aversion to cold<br>           ■ id = "1"<br>         - mild fever<br>           ■ id = "1"<br>         - no sweat<br>           ■ id = "1"<br>         - headache<br>           ■ id = "1"<br>         - sore limbs<br>           ■ id = "1"<br>         - stuffy nose, runny nose<br>           ■ id = "1"<br>         - sneezing<br>           ■ id = "1"<br>         - pharynx<br>           ■ id = "1"<br>         - severe cough<br>           ■ id = "1"<br>         - thin, pale complexion<br>           ■ id = "1"<br>      - related symptoms<br>         - not thirsty<br>           ■ id = "1"<br>         - prefer hot drinks<br>           ■ id = "1"<br>    - tongue surface<br>      - thin, white<br>        ■ id = "1"<br>    - pulse<br>      - floating<br>        ■ id = "1"<br>      - rapid<br>        ■ id = "1"<br>    - wind-heat syndrome<br>         - mild aversion to cold<br>           ■ id = "1"<br>         - high fever<br>           ■ id = "1"<br>         - sweating<br>           ■ id = "1"<br>         - severe headache<br>           ■ id = "1" | Heat in the palms | Joint pain |
| | Normal stool | Normal urination |
| | Lack of appetite | Dull chest pain |
| | Little night sweat | Ears and eyes |
| | Lung cough | Little white sticky sputum |
| | Pain<br>Chest | Pale complexion |
| | Sleeplessness | Dull pain |
| | Stuffy nose, sneezing | Thirsty |
| | Pharynx | Acidic food |
| | Mental state | |
| | Tongue | |
| | [illegible] | |
| | Thin, yellowish fur | |
| | Dry and reddish (tongue) | |
| | Little fur | |
| | Thin fur | |
| | Yellowish fur | |
| | Little fur or yellowish fur | |
| | Grey | |
| | [illegible] fur | |
| | Pulse | |

Figure 4

| | | |
|---|---|---|
| - Edema<br>  - Yang-edema<br>    - Wind-water overflow<br>      • symptoms<br>        • swollen eyes and face<br>          • id = "1"<br>        • limbs and the whole body swell<br>          • id = "1"<br>        • aversion to wind<br>          • id = "1"<br>        • sore limbs and joints<br>          • id = "1"<br>        • difficulty in urination<br>          • id = "1"<br>  - tongue surface<br>    - thin, white<br>      • id = "1"<br>  - pulse<br>    - floating<br>      • id = "1"<br>    - rapid<br>      • id = "1"<br>- Ulcer<br>  - symptoms<br>    • swollen eyes and face<br>      • id = "1"<br>    • limbs and the whole body swell<br>      • id = "1"<br>    • difficulty in urination<br>      • id = "1"<br>    • sore throat<br>      • id = "1"<br>    • aversion to wind<br>      • id = "1" | Severe aversion to cold | |
| | Fever | Limbs and the whole body swell |
| | Normal stool | Difficulty in urination |
| | Diet | Chest and abdomen |
| | Sore limbs after sweat | Eyes and ears |
| | Cough, little sputum | Thick, yellowish sputum |
| | Pain | Forms |
| | Body parts | |
| | Sleeplessness | Pale facial completion |
| | Stuffy nose, runny nose | Chapped lips |
| | Sore throat | Vomit acidic-smelly food |
| | Normal mental state | |

Figure 5A

| ILLNESS | SCORE |
|---|---|
| Yang-water: wind-water overflow | 5 |
| Ying-water: ulcer toxic inside body | 4 |
| Headache: liver-yang pain | 2 |
| Flu: wind-cold syndrome | 1 |
| Purplish mark: blood syndrome | 1 |
| Asthma | 1 |
| Cough, wind-cold syndrome | 1 |
| Sputum, drink | 1 |
| Spleen symptoms, hot spleen | 1 |
| Headache: wind-heat headache | 1 |
| Drink: spleen-stomach yang deficiency | 1 |
| Headache: wind-wet headache | 1 |
| Ying deficiency | 1 |
| Joint: joint | 1 |
| Stomachache: cold in the stomach | 1 |
| Palpation: timid | 1 |
| Stomachache: Qi-lagging syndrome | 1 |

Figure 5B

- Ulcer toxicity inside the body
    - symptoms
        - swollen eyes and face
            - id = "1"
        - limbs and the whole body swell
            - id = "1"
        - difficulty in urination
            - id = "1"
        - ulcer
            - id = "1"
        - aversion to wind
            - id = "1"
        - fever
            - id = "1"
    - tongue surface
        - reddish tongue
            - id = "1"
        - thin, yellowish tongue
            - id = "1"
    - pulse
        - floating
            - id = "1"
        - slippery
            - id = "1"

Figure 6

ONTOLOGICAL INFORMATION RETRIEVAL SYSTEM

CROSS REFERENCE TO A RELATED APPLICATION

This application is a National Stage Application of International Application Number PCT/IB2010/002237, filed Jul. 29, 2010; which claims the benefit of U.S. provisional application Ser. No. 61/229,545, filed Jul. 29, 2009, which are incorporated herein by reference in their entirety.

BACKGROUND OF THE INVENTION

Traditional Chinese Medicine (TCM) is enshrined in the local law of the Hong Kong SAR. For this reason computer-aided clinical TCM practice has become a quest for many people. One of these quests is to retrieve herbs with respect to their temperament and curative effects.

Ontology can be used to organize TCM practice. Ontology is a data model that represents a set of concepts within a domain and the relationships between those concepts. Ontology is used to reason about the objects within that domain.

For example, for a query of Q{x, y} the retrieved result should be a conclusion by inference with the two actual parameters x and y. The process of conclusion by inference is called parsing and the piece of software or computational logic used to achieve this conclusion is referred to as a parser. The combination of "query+semantic net+ontology" is the basis of a telemedicine system, which administers medicine over a network, such as the Internet. Telemedicine refers to administering medicine or medical information over a network that supports wireless and wireline communication. For example, a telemedicine environment may be made up of many mobile and/or stationary clinics that collaborate wirelessly. Each clinic includes a clinical telemedicine diagnosis/prescription system that can be operated by a physician, and a pharmacy. A physician can treat patients locally by using the clinical telemedicine diagnosis/prescription system.

TCM is highlighted here as an illustrative example of a domain that can be represented and accessed via an ontological information retrieval system. The subject invention can also be applied to other domains.

BRIEF SUMMARY OF THE INVENTION

The present disclosure relates to an ontological information retrieval system utilizing a three layer architecture. According to one embodiment of the invention, an ontological information retrieval system is provided that represents an ontological layer in an annotated form, represents the annotated form of the onotological layer as a document object model (DOM) tree for parsing the data, and utilizes a graphical user interface (GUI) to represent the DOM tree for human understanding and manipulation. Other human interfaces to the DOM tree can be used with the subject invention as will be apparent to one skilled in the art.

In accordance with the present invention, a DOM tree containing attributes and their associations is provided for establishing a semantic network to parse the ontological data. A query can be mapped into a semantic and the DOM searched to find instances of that semantic.

A specific embodiment of the subject ontological information retrieval system can be utilized for computer-aided clinical TCM practice. In one implementation, a user can input a query with symptoms determined from a patient, and the system's parser can find instances of the symptoms in the DOM tree. The instances can be communicated to the user by, for example, highlighting the instances of the symptoms in the DOM tree displayed to the user.

A relevance index (RI) can be further provided for evaluating a diagnosis by comparing the symptoms determined from a patient with the expected symptoms of the diagnosed illness and returning a value based on the number of matched symptoms.

A frequency index (FI) can be further provided for evaluating a diagnosis by comparing the symptoms determined from a patient with the expected symptoms of the diagnosed illness with additional weighting for the major symptoms of the illness. The FI takes into consideration the importance of a symptom, which can include categories such as major criteria and minor criteria of an illness.

BRIEF DESCRIPTION OF THE DRAWINGS

FIG. 2 shows a GUI of a sample parser in accordance with an embodiment of the present invention.

FIG. 3 shows a GUI of a system in accordance with an embodiment of the present invention.

FIG. 4 shows a GUI for selection of symptom attributes in accordance with an embodiment of the present invention.

FIGS. 5A and 5B show a GUI for presenting matched symptoms and sorted results for an example in accordance with an embodiment of the present invention. FIG. 5B shows a close-up of the data grid for the sorted relevance index of the GUI illustrated in FIG. 5A.

FIG. 6 shows a close-up of a GUI presenting a selection result for explaining a verification method in accordance with an embodiment of the present invention.

DETAILED DISCLOSURE OF THE INVENTION

Figure 1:
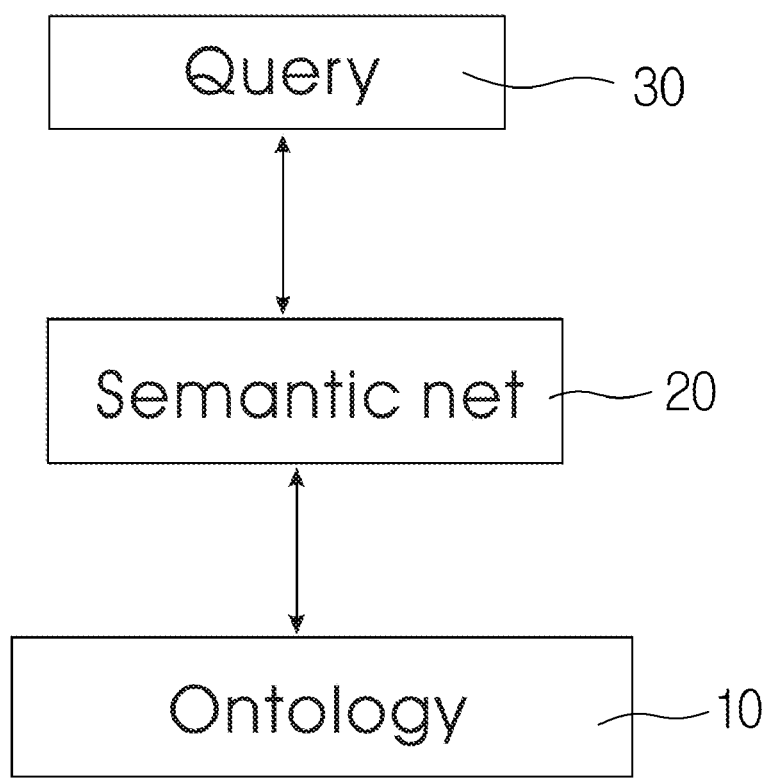
FIG. 1 shows a block diagram of a 3-layer architecture for an ontological information retrieval system in accordance with an embodiment of the subject invention.

An ontological information retrieval system is provided. The subject ontological information retrieval system can utilize a three-layer architecture for transitive mapping. FIG. 1 shows a block diagram representation of the three-layer architecture. The bottom layer is the ontological layer 10 providing the ontological information. In certain embodiments of the present invention, the ontological information can be provided in annotated form. For example, Extensible Markup Language (XML) can be used to represent the ontological information. The middle layer provides the semantic net 20, which is the machine-processable form (e.g., machine language of a processor) of the ontological layer 10. The semantic net 20 utilizes logic representations for all the information of the ontological layer 10. For example, attributes and their associations can be represented. The logic representation of the semantic net 20 can be referred to as a Document Object Model (DOM) tree. The DOM tree can be used to parse the ontological layer 10. For example, the DOM tree can be used to map a query (e.g. Q{x,y}) from the top layer 30 into a semantic. Therefore, a semantic in the DOM tree can be found by tracing a semantic path. The top layer (query layer 30) provides the syntactical representation of the semantic net 20 for human understanding in the form of a system of queries.

For a perfectly mapped system, the three layers are transitive. That is, when an element in the query layer 30 is related to an element in the semantic net layer 20, and the element in the semantic net layer 20 is related to an element in the ontology layer 10, then the element in the query layer 30 is related to the element in the ontology layer 10.

The subject ontological information retrieval system can be applied to a telemedicine system. In such an embodiment, the ontological information can relate to, for example, TCM. Accordingly, the ontological layer 10 can include available TCM formal information obtained from the classics and treatises on the subject (also referred to as TCM vocabulary). The representation of this information can be provided in annotated form by using metadata such as XML. The ontological layer 10 is represented with a DOM (semantic net 20) configured in accordance with an embodiment of the present invention, and the query layer 30 is provided in the form of a graphical user interface (GUI).

Aspects of the invention may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention. In addition, computer systems, servers, work stations, and other machines may be connected to one another across a communication medium including, for example, a network or networks.

In accordance with the present diclsosure, computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

In accordance with certain embodiments of the present invention, a system including one or more processors, memory, a display, and an input device is provided for retrieving ontological information and providing that information to a user by using the three-layer architecture as described with respect to FIG. 1. All or portions of the ontological layer 10 can be stored in the memory of the system. The semantic net 20 can be implemented as computer-readable (processor-readable) instructions stored in the memory of the system. The query system 30 can be provided in the form of a GUI displayed on the display of the system. A user can manipulate and interact with the GUI by using the input device.

For a telemedicine application, the semantic net 20 is the machine processable form of the TCM ontological layer and the GUI for the query system 30, which abstracts the semantic net, is utilized for human understanding and manipulation. The symptoms that are keyed-in via the GUI are captured as actual parameters for the query to be implicitly (user-transparently) constructed by the GUI system as input to the parser. The parsing mechanism draws the logical conclusion from the DOM tree (e.g., the corresponding illness for the query). The ontological layer 10 defines the bounds of the diagnosis/prescription operation. The ontological layer is the vocabulary and the operation standard of the system.

For embodiments utilizing XML for the ontological layer, the parser can be established using a software language such as VB.net (Visual Basic for the Internet) and compiled into machine readable code.

A GUI of a sample parser according to one embodiment is shown in FIG. 2. The sample parser can match an attribute with the XML annotation and display the matches for the query. For example, instances of symptoms input into the query can be displayed. In a specific embodiment, the parser can convert an XML annotation into a DOM tree and highlight the parameters that were input in the query. The parser shown in FIG. 2 does not return the conclusion, but embodiments are not limited thereto. In a further embodiment, the parser can return the conclusion. For example, the relevant illness name and type can be highlighted or displayed to the user after inputting a query indicating symptoms of an illness.

In yet a further embodiment, a relevance index (RI) can be incorporated to enable a user to evaluate the results. For example, the RI can be calculated based on frequency (i.e., the number of matched symptoms.

As another embodiment, a frequency index (FI) can be used to improve the RI calcualation by incorporating weighting factors. For example, for each disease type, the symptoms can be categorized and weighted. FIG. 6 shows a result of a search. The symptoms were categorized as major (主症), minor (兼症), tongue surface (舌苔) and pulse (脈象). Each symptom is also assigned a weight, eg: 0.5 for main symptoms, 0.3 for accompanies and 0.1 for both tongue surface (tongue analysis) and pulse (heart rate). If the case only describes symptoms that do not include main and accompany symptoms, those symptoms are viewed as main symptoms. The calculating method is listed below for the result shown in FIG. 6:

Main Symptoms:
All symptoms=7, Matched symptoms=3, ratio=0.5

$$FI=3/7*0.5=0.21$$

Tongue Surface Symptoms:

$$FI=0/2*0.1=0$$

Pulse Symptoms:

$$FI=0/2*0.1=0$$

Total FI score=0.21+0+0=0.21

Relevance score based on frequency=3

The FI score gives the biggest ratio or weight to major symptoms due to their importance. In contrast, the RI score is based only on frequency. The FI score can be advantageous in certain situations because when the score is based on only frequency, the disease which has more matched symptoms that are minor or in pulse would appear to be a better match, and a disease that has less matches, but scored the most in the main symptoms may be inadvertently missed.

Following are examples that illustrate procedures for practicing and understanding the invention. These examples should not be construed as limiting.

Example 1—XML Annotation of Ontological Layer

Appendix A shows a sample disease, the common cold, annotated with an XML tree. The general structure for the XML annotation of TCM follows the following framework.

```
- <disease>
    <proof_of_disease>
    <syndrome differentiation>
    <meridian A>
        <symptom>
    <meridian B>
        <symptom>
```

An example of the XML annotation for 38 illnesses is shown in Appendix C, as disclosed in U.S. provisional application Ser. No. 61/229,545, filed Jul. 29, 2009, which is incorporated herein by reference in its entirety.

The structure shown can be used to represent ontological information for TCM. But other structures may be used and other domains may be represented and accessed using an ontological information retrieval system.

Example 2—TCM Information Retrieval

According to one embodiment, an ontological information retrieval system is implemented to identify all the symptoms (query attributes) with respect to the "10 questions" (十問歌). In particular, the list of 21 identifications is as follows: TCM [中醫內科學]: chills and fever [寒熱], head and body [頭身], fecal [大便], urine [小便], diet [飲食], thoracoabdominal [胸腹], sweat [汗], hearing/vision [耳目], cough [咳], sputum [痰], pain (location, form) [痛(部位，形式)], sleep [睡眠], complexion [面色], nose [鼻], lips [口唇], throat/pharynx [啊咯], vomit [嘔吐], mental status [精神], menses [經期], vaginal discharge [帶下], tongue [舌], surface or tongue [苔].

These 21 basic symptoms for "十問歌" are tabulated in the tables of Appendix B from Tables 1A to 1D. Table 1E provides a summary of the Symptoms identified based on the "10 questions (十問歌)".

An XML annotation was created for 38 chosen illnesses from some established TCM classics. The XML annotation of these 38 illnesses is shown in Appendix C, as disclosed in U.S. provisional application Ser. No. 61/229,545, filed Jul. 29, 2009, which is incorporated herein by reference in its entirety. When the XML annotation is input to the parsing mechanism such as shown in FIG. 2 the XML annotation is displayed as a DOM tree. The GUT of the parser also allows the user to input a query with symptoms. Then, the parser can find these symptoms and highlight them on the DOM tree. Alternatively, the parser can return a disease conclusion, a relevance index, or a frequency index as discussed above.

The XML annotation in Appendix C for the 38 illnesses includes the 21 symptoms as their attributes. Together they form the subsumption hierarchy that lets symptoms associate with illnesses.

When the RI is incorporated, the system user, such as a physician, can evaluate the diagnosis. For example, if the physician obtained only two symptoms from the "10 questions (十問歌)," but the classical information shows that there could be 10 symptoms all together. Then, the RI is the score for the quality of the diagnostic process.

To reduce search time in embodiments where the sample parser program matches symptoms by loading the data and then searching the data, the loading of the data (such as a Display Disease XML) can be separated from the searching so that subsequent searches can utilize the same loaded data. FIG. 3 shows the separate functions. The loaded Disease XML tree is the annotated form of the ontological layer (bottom layer) and the parser program loads the XML tree as a DOM tree.

The physician can select the symptoms attributes by clicking the combo boxes shown in the GUI. The symptom attributes are extracted based on the TCM vocabulary and Table 1A to 1D of Appendix B. After the symptoms attributed are selected, the program matches the attributes with the XML annotation of 38 illnesses once the search button is clicked as shown in FIG. 4. The disease XML annotation shown in the figure is for all internal illnesses. Below each illness, there are nodes describing the symptoms. The node can be highlighted, in yellow for example, if it is correctly matched with the input symptoms attributes.

Since some symptoms of different diseases may be the same, the relevance index of each illness is calculated. The relevance of the matched attributes can be measured for the diagnostic process (basic: frequency).

In one embodiment, a 2D array can be used to store the matched symptoms and disease name and the number of matched symptoms can be calculated to determine as their scores. The disease name and score is passed to another 2D array and then sorted.

In another embodiment; a datatable, which is a VB.net object for storing data in a table format, can be used. The data stored in the table format can then be placed into the data. Grid. For example, the VB.net object data table can store the illness names that have symptoms matched and the RI, which is calculated by the number of matched symptoms.

Example 3—Matched Symptoms and Sorted Results

FIGS. 5A and 5B illustrate an example symptom query and results. In particular, after inputting symptoms, the display indicates the following:

Yang edema—wind edema flooding (陽水 — 風水泛濫) has five highlighted matched symptoms, so the relevance index is 5.

Headache—liver yang headache (頭痛 — 肝陽頭痛) has two matched symptoms so the relevance index is 2. Here, the relevance index is based on the number of matched symptoms.

The result shows that the patient is more likely to catch Yang edema—wind edema than a Liver yang headache. The sorted index is for physician's reference.

Example 4—Methodology Base

The UMLS (Unified Medical Language System) is a medical ontology for allopathic applications and is intrinsically suitable for textual mining. It aims to resolve the difference in terminologies among different incompatible medical systems. The semantic groups in level 1 represent the different domains of query (e.g. TCM diagnosis). Level 2 is the semantic net to formally give one unique answer to a specifically formulated query. Level 3 is the ontological infrastructure for the "global allopathic view," which is described by Jackei H. K. Wong in "A Concise Survey by PhraPharm on Data Mining Methods," (2008), which is incorparated by reference herein in its entirety.

In addition to text mining, automatic semantic aliasing support can be included in the evolution of the ontology as described by Jackei H. K. Wong et al. in "Real-Time Enterprise Ontology Evolution to Aid Effective Clinical Telemedicine with Text Mining and Automatic Semantic Aliasing Support," Proceedings of the OTM (Nov. 9-14, 2008), Vol. 5332 Lecture Notes in Computer Science; (2008), which is incorporated by reference herein in its entirety.

For example, TCM ontology was built based on all the canonical texts. A physician extracts a list of symptoms for a patient with a rigid diagnostic procedure. This list of symptoms is then matched with those extracted from canonical texts in the form of descriptors for different diseases. The different matches would have varying relevance. A relevance (index) of 0.7 (70%) to Cough, for example, indicates that the patient's sickness has 70% likelihood to the Cough context. That is, it could betreated with recipes for Cough. Then, the rest 30% difference could mean one of the following:

a) if the symptoms for the 30% are "minor" or "tongue surface" or "pulse" then the patient's sickness X is perhaps just Cough.

b) If the symptoms for the 30% are "major" then "although the sickness X can be treated like Cough in the beginning but the sickness may not be Cough.

c) What follows the second point above include: i) the extraction from the canonical texts to build the different descriptors for the TCM ontology is flawed; sickness X was a miss, and ii) sickness X is a new form of disease, which was never recorded canonically and therefore a discovery.

The discovery can then be recorded formally to become part of the revised canonical information. Thus, such a system can build on itself to expand the ontological domain.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

APPENDIX A

```
<?xml version="1.0" encoding="Big5" Cold Disease XML Tree?>
- < flu>
- < cold / Wind-cold syndrome>
- < main symptoms>
- < appearances>
- < aversion to cold>
  < severe aversion to cold>id="1"</ severe aversion to cold>
    </ aversion to cold >
- < fever>
  < low fever>id="1"</ low fever>
    </ fever>
- < sweat>
  < no sweat>id="1"</ no sweat>
    </ sweat>
- < head and body>
  < headache and sore limbs>id="1"</ headache and sore limbs>
    </ head and body>
    </ appearances>
- < lungs>
- < nose>
  < runny nose>id="1"</ runny nose>
    </ nose>
- < pharynx>
  < itchy throat>id="1"</ itchy throat>
    </ pharynx>
- < cough>
  < cough and heavy voice>id="1"</ cough and heavy voice>
    </ cough>
- < sputum>
  < thin, white sputum>id="1"</ thin, white sputum>
    </ sputum>
    </ lungs >
    </ main symptoms>
- < related symptoms>
  < not thirsty or thirsty and prefer hot drinks>id="1"</ not thirsty or thirsty and prefer hot drinks >
    </ related symptoms>
- < surface of tongue / fur>
  < thin, white fur>id="1"</ thin, white fur >
    </ surface of tongue / fur >
- < pulse >
  < floating and/or rapid pulse>id="1"</ floating and/or rapid pulse >
    </ pulse>
    </ Wind-cold syndrome>
- < Wind-heat syndrome>
- < main symptoms>
- < appearances>
- < aversion to cold>
  < slight aversion to cold>id="2"</ slight aversion to cold>
    </ aversion to cold>
- < fever>
  < high fever>id="2"</ high fever>
    </ fever>
- < sweat>
  < sweat>id="2"</ sweat>
    </ sweat>
- < head and body>
  < swelling pain in the head>id="2"</ swelling pain in the head>
    </head and body>
    </ appearances>
- < lungs>
- < nose>
  < nasal congestion and sticky and yellow nasal fluid>id="2"</ nasal congestion and sticky and yellow nasal fluid>
    </ nose>
- < pharynx>
```

APPENDIX A-continued

```
< pain and swelling in the throat / pharynx>>id="2"</ pain and
    swelling in the throat / pharynx>
    </ pharynx>
- < cough>
< cough, coarse voice, rapid breathing >id="2"</ cough, coarse
    voice, rapid breathing>
    </ cough>
- < sputum>
< sticky sputum in yellowish or white color>id="2"</sticky sputum
    in yellowish or white color>
    </ sputum>
    </ lungs>
    </ main symptoms>
- < related symptoms>
< thirsty and prefer to drink>id="2"</ thirsty and prefer to drink >
    </ related symptoms>
- < surface of tongue / fur >
< thin, white and dry tongue surface or thin, white, and reddish
    around the edge of the tough surface>id="2"</ thin, white and
    dry tongue surface or thin, white, and reddish around the edge of
    the tough surface >
    </ surface of tongue>
- < pulse>
< floating pulse>id="2"</ floating pulse>
    </ pulse>
    </ wind-heat syndrome>
- < summer-heat dampness syndrome>
- < main symptoms>
- < appearances>
- < aversion to cold>
< slight aversion to cold>id="3"</ slight aversion to cold>
    </ aversion to cold>
- < fever>
< fever in the body>id="3"</ fever in the body>
    </ fever>
- < sweat>
< little sweat>id="3"</ little sweat>
    </ sweat>
- < head and body>
< dizziness and swelling pain in the head, sore limbs>id="3"</
    dizziness and swelling pain in the head, sore limbs >
    </ head and body>
    </ appearances>
- < lungs>
- < nose>
< runny nose and sticky nasal fluid>id="3"</ runny nose and sticky
    nasal fluid >
    </ nose>
- < pharynx>
< sore throat>id="3"</ sore throat>
    </ pharynx>
- < cough>
< cough>id="3"</ cough>
    </ cough>
- < sputum>
< sticky sputum in white or yellow color>id="3"</ sticky sputum in
    white or yellow color>
    </ sputum>
    </ lungs>
    </ main symptoms>
- < related symptoms>
< thirsty and vexation >id="3"</ thirsty and vexation >
    </ related symptoms>
- < surface of tongue / fur >
< yellow or yellow greasy moss fur>id="3"</ yellow or yellow
    greasy moss fur>
    </ tongue surface / fur>
- < pulse>
< thin pulse>id="3"</ thin pulse>
    </ pulse>
    </ summer-heat dampness syndrome>
    </ flu / cold>
```

Appendix B

TABLE 1A

5 symptoms

| Wind-cold syndrome | Head and Body | Stool | Urine | Diet |
|---|---|---|---|---|
| Severe aversion to cold | Headache | Loose stool | Reddish and short urination | Not thirsty |
| Mild aversion to cold | Sore and pain in the limbs | Diarrhea before dawn | Dysuria | Prefer cold drinks |
| Slight aversion to cold | Swelling pain in the head | Loose stool | Poor urine flow | Thirsty and want to drink |
| Low fever | Dizziness and swelling pain in the head | Constipation | Yellowish and reddish urine | Irritable and thirsty |
| High fever | Aching pain in limbs | Constipation; hard stool | Lack of urine or stool | Thirsty but do not want to drink |
| Fever in the body | Chest and hypochondriac pain | Constipation; reddish stool | Incontinence | Slimy mouth |
| No fever | hypochondriac pain | Poor stool | Yellowish and reddish urine | Dry mouth and want to drink |
| Tidal fever | Weight loss and fatigue | Constipation | Loose stool | Prefer hot drink |
| Easy to catch cold | Weight loss | Constipation | Incontinence | Low appetite |
| Aversion to cold | Cold limbs | Dark stool | Dry stool | Eat little |
| Fever in the palm and feet in the afternoon | Body pain | Constipation and yellowish urine | Loose stool | Vexation and prefer hot drinks |
| Tidal fever in the afternoon | Swollen body | Constipation and no urine | Reddish urine | Thirsty but do not want to drink |
| Tidal fever; always feel cold | Swollen feet | incontinence | Short urine flow and yellowish urine | Thirsty |

TABLE 1A-continued

| | | 5 symptoms | | |
|---|---|---|---|---|
| Wind-cold syndrome | Head and Body | Stool | Urine | Diet |
| Tidal fever in the afternoon | Cold fever and back pain | Incontinence | Dysuria | Eat little but feel full |
| Aversion to cold and wind | Lumber pain | Constipation | Loose stool | Vexation and taste bitter |
| Aversion to cold with fever | Body Shivering | Dry stool | Little urine flow | Faint after eat and drink too much |
| Fever; sometimes sweat sometimes no sweat | Aversion to cold with cold body | Constipation | Short urine | Thirsty and want to drink |
| Low fever | Swollen lower body | Hard-bound stool | Difficult urination | Reduced food intake |
| Fever | Lumbar pain | Constipation | Urination with stone | Thirsty and have hard-bound stool |
| Aversion to cold | Dizziness and headache | Loose stool | Pain during urination | Cannot swallow |
| Fever | Dizziness and blurry vision | Hard-bound stool | Urination with blood | Cannot Swallow |
| Easy to catch a cold | Dizziness | Diarrhea before dawn | Urination with blood | Loss of appetite |
| Sometimes feel cold and sometimes feel hot | Cold in the body and limbs | No stool | Reddish blood | Thirsty and want to drink |
| Aversion to cold; lack of energy | Dizziness | Loose stool | Turbid urine | |
| Aversion to cold and wind | Fatigue | Constipation | Poor urine flow | Vexation and thirsty |
| Aversion to cold with high fever | Aversion to cold and cold limbs | Constipation | little urination | Eat little |
| Mild aversion to cold with high fever | Cold extremities and sweating | Hard-bound stool | Congestion | Fever and thirsty |
| Severe aversion to cold with low fever | Fatigue and short breathing | Difficulty in passing stool | Difficulty with urination | Loss of appetite |
| | Pain in shoulder back; left arm | Difficulty in passing stool | | High fever, vexation, and thirsty |
| Aversion to cold | Palpitation and lumber aching pain | Stool contains mucus | Fatigue during passing stool | Not thirsty |
| Aversion to wind | Lumbago aching pain and legs sore | Dry stool | Frequent urination | Thirsty but do not and want to drink |
| Fever | Fatigue in limbs | Loose stool | Frequent urination | Vexation and want to drink water |
| Aversion to cold | Fatigue and lack of energy | Diarrhea | Tubid urine | Rapid digestion of food and susceptible to hunger |
| Alternations in chills and fever | Numbness in skin | Yellowish, smelly stool | Sweet | Hungry but lack of appetite |
| Cold in the body and limbs | Fatigue in the body and limbs, joint pain | Diarrhea | Clear urine | Thirsty but do not want to drink |
| Body heat | Joint swollen | Smelly stool | Turbid as cream | Thirsty but do not want to drink |
| Tidal fever | Long-term fatigue | Sloppy stool | Enuresis | Loss of appetite |
| Alterations in cold and fever | Swelling joint | Diarrhea due to indigestion | Clear urine | Fever and thirsty |
| Aversion to cold | Deformity | Stool sometimes hard-bound sometimes watery | Frequent urination and clear urine | Diarrhea and do not want to drink |
| Fever | Fatigue | Difficulty in passing stool | Clear urine | Lack of appetite |
| Aversion to cold with fever | Aching pain in the entire body | Dry stool | Short urine flow and yellowish urine | Lack of appetite |

TABLE 1A-continued

| | 5 symptoms | | | |
|---|---|---|---|---|
| Wind-cold syndrome | Head and Body | Stool | Urine | Diet |
| Cold in the body and limbs | Facial and lower extremity edema | Difficulty in passing stool | | Lack of appetite |
| Aversion to cold and prefer warm | face, neck, chest and arm with blood mole | | | Lack of appetite |
| | Red palm | | | Abdominal distention and lack of appetite |
| | Make a fist | | | Vexation and do not feel thirsty |
| | Cold extremities | | | Belching and lack of appetite |
| | Headache | | | Belching and lack of appetite |
| | Limb tremor | | | Abdominal distention and lack of appetite |
| | Twitching limbs | | | Poor digestive ability |
| | Frequent headahce | | | Thirsty but do not want to drink |
| | Headache | | | Feel hungry but do not want to drink |
| | Swelling headache | | | Not thirsty |
| | Cracking headache | | | Lack of appetite |
| | Headache | | | |
| | Drowsiness and fatigue | | | |
| | Headache and blurry vision | | | |
| | Abdominal pain | | | |
| | Lumbago pain | | | |
| | Headache and dizziness | | | |
| | headache | | | |
| | Long-term headache | | | |
| | Lumbar and knees aching pain | | | |
| | Hemiplegia | | | |
| | Cold extremities | | | |
| | Facial muscle convulsion | | | |
| | Numbness of extremities | | | |
| | Hemiplegia | | | |
| | Fever and body contracture | | | |
| | Joint pain | | | |
| | Headache and dizziness | | | |
| | Sore limbs | | | |
| | Two hands Make a fist | | | |
| | Body convulsion | | | |
| | Cold extremities | | | |
| | Fatigue in th body and limbs | | | |
| | Cold extremities | | | |
| | Headache | | | |
| | Hongre head | | | |
| | Oppression in the chest and hypochondria distention pain | | | |
| | hypochondria distention pain | | | |
| | Lumbar aching | | | |

TABLE 1A-continued

| 5 symptoms | | | | |
|---|---|---|---|---|
| Wind-cold syndrome | Head and Body | Stool | Urine | Diet |
| | pain | | | |
| | Lumbar aching pain and headache | | | |
| | Fatigue in legs | | | |
| | Fatigue | | | |
| | Bone and joint aching pain | | | |
| | Headache and body pain | | | |
| | Cold extremitites | | | |
| | Drowsiness and body ache | | | |
| | Hypochodrium pain with distention | | | |
| | Body and limbs swelling | | | |
| | Body sore | | | |
| | Body fat traumata | | | |
| | Whole body edema | | | |
| | Fatigue | | | |
| | Whole body swell | | | |
| | Cold extremities | | | |
| | Lumbar aching pain | | | |
| | Lumbar aching pain | | | |
| | Lumbar and joint aching pain | | | |
| | Lumbar and joint cold | | | |
| | Sore limbs | | | |
| | Lumbar aching pain | | | |
| | Legs sore | | | |
| | Dizziness | | | |
| | Hypochondrium pain and limbs convulsion | | | |
| | Exposed vein | | | |
| | Cold extremitites | | | |
| | Lie down a curl | | | |
| | Lumbar and joint cold | | | |
| | Anus burning pain | | | |
| | Fatigue | | | |
| | Dry skin | | | |
| | Weight loss | | | |
| | Anus burning pain | | | |

TABLE 1B

| 4 symptoms | | | |
|---|---|---|---|
| Chest and abdominal | Sweat | Ear and eye | Cough |
| chest oppression | No sweat | Dizziness | Cough and coarse voice |
| want to vomit | Sweat | | Coarse voice |
| stomach stuffiness | Little sweat | Dizziness | Rapid breathing |
| Dull and oppressive pain in the chest | Night sweat | Tinnitus | Cough |

TABLE 1B-continued

| 4 symptoms | | | |
|---|---|---|---|
| Chest and abdominal | Sweat | Ear and eye | Cough |
| Chest and hypochondrium pulling pain or stabbing pain | Easy sweat | Dizziness | Heavy and strong voice |
| Abdominal distention pain | Little night sweat | Dizziness and tinnitus | Cough |
| Chest pain and difficulty in breathing | Sweating during sleep | Reddish eyes and tinnitus | Rough voice and cough |
| Oppressive pain the chest | A combination of spontaneous sweat and night sweat | Dizziness | Cough |
| Oppressive pain the chest | Spontaneous sweat | Dizziness and tinnitus | Cough and coarse voice |
| Dyspnea and cannot lay down | Spontaneous sweat and do not want to speak | Yellowish skin and facial complexion | Cough and rapid breathing |
| Chest and hypochondrium dull pain | Cold sweat | Reddish eyes | Cough |
| Chest pain | Sweat and aversion to wind | Sunken eyes | Noisy cough |
| Hypochondrium distention | Spontaneous sweat or night sweat | Sunken eyes | Dry cough |
| Cardiff fullness | Sweat | Look up | Short cough |
| Cardiac chest pain | Sweat and cold limbs | Mouth and eyes suddenly on the side of the cheeks | Coarse voice |
| Abdominal distention | Spontaneous sweat and cold skin | Dizziness and tinnitus | Cough in a low voice |
| There is sound of water in the abdominal/stomach | Profuse sweat | Close eyes | Rapid breathing |
| Water in the intestine | Profuse sweat | Reddish eyes | Cough and rapid breathing |
| Stomach distention prefer warm food, aversion to cold food | Rapid breathing and spontaneous sweat | Yellowish skin and eyes | Loud wheezing |
| Chest pain | | Blurry vision | Lung cough |
| Chest tightness and retching | | Yellowish skin and eyes | Cough and rapid breathing |
| Stomach full | | Swelling face and eyes | Cough and fatigue |
| Palpation | | Dry ears | Rapid breathing |
| Cardiac chest pain from time to time | | Dizziness | Cough and rapid breathing |
| chest tightness and irritability | | Blurry vision | Cough and rapid breathing |
| Chest tightness and rapid breathing | | Reddish face | Little cough |
| Chest and abdominal distention | | | Reduced coughing |
| stabbing pain in the chest | | | Cough |
| Chest pain or cramps | | | Wheezing and rapid breathing |
| Chest pain | | | Cough and rapid breathing |
| Chest tightness and chest pain | | | Rapid breathing |
| Chest tightness and chest pain (dull) | | | Palpitation and wheezing |
| Irritability and chest tightness, chest pain | | | Cough and wheezing |
| Chest pain | | | Cough |
| Palpitation and chest pain | | | |
| Chest tightness and palpitation | | | |
| Chest tightness | | | |
| Vomit | | | |
| Belch | | | |
| Chest tightness and belch | | | |
| Abdominal distention | | | |
| Abdominal distention | | | |
| Belch | | | |
| Abdominal distention | | | |
| Abdominal distention | | | |
| Abdominal distention | | | |
| Hot | | | |
| Abdominal distention and discomfort | | | |

TABLE 1B-continued

| 4 symptoms | | | |
|---|---|---|---|
| Chest and abdominal | Sweat | Ear and eye | Cough |

Abdominal distention
Abdominal distention and discomfort
Exposed veins
Abdominal distention
Chest tightness
Chest tightness
Abdominal distention and chest tightness
Chest tightness and vomit
Chest tightness and discomfort
Chest tightness and chest pain
Chest tightness and abdominal distention
Diarrhea
Hypochondrium and abdominal distention
Abdominal distention
Lower abdominal distention
Lower abdominal pain
Lower abdominal distention and pain
Lower abdominal distention and pain
Chest tightness and pain
Gas coagulation in the stomach
Abdominal distention
Abdominal pain
Sudden abdominal pain
Chronic abdominal pain
Abdominal or hypochodrium distention pain
Abdominal stabbing pain
Acute abdominal pain
Lower abdominal pain
Chest tightness and belch
Chest tightness, abdominal distention and belch
Abdominal distention
Abdominal pain
Abdominal distention and pain
Abdominal pain
Abdominal pain before passing stool
Chest tightness, abdominal distention
Stomach burning pain
Abdominal pain
Abdominal distention and discomfort
Chest tightness and pain
Chest tightness
Chest tightness

TABLE 1C

| 5 symptoms | | | | |
|---|---|---|---|---|
| Pain | Sleep | Facial complexion | Nose | Mouth and lip |
| Headache | Restless and insomia | Fever and reddish facial complexion | Runny nose | Purplish lip |
| Limbs sore | Nightmare | Cough and reddish facial complexion | Sneezing | Purplish lip |

TABLE 1C-continued

| | | 5 symptoms | | |
| --- | --- | --- | --- | --- |
| Pain | Sleep | Facial complexion | Nose | Mouth and lip |
| Distention pain in the head | Sleepless with nightmare | Pale facial complexion and aversion to wind | Sluffy nose and sticky nasal fluid | Lip pale |
| headache | Insomia | Reddish facial complexion and irritable | Sneezing with sticky nasal fluid | Purplish lip |
| Limbs and body sore | Irritable and sleeplessness | Pale facial complexion | Dark reddish tongue | Purplish lip |
| Chest and hypochondrium pain | Anxious, irritable and sleeplessness | Reddish facial complexion | Nose and teeth bleeding | Pale lip |
| Hypochondrium pain | Chest tightness, irritable, sleeplessness | Reddish facial complexion | Rapid breathing | Dry mouth |
| Fever and back pain | Abdominal discomfort and sleeplessness | Pale facial complexion | Weak breath | Open mouth |
| Lumbar pain | Palpitation, irritable, and sleeplessness | Pale facial complexion | Dyspnes | Lip in dark color |
| Pain | Nightmare and easily waked up | Pale facial complexion | Stuffy nose | Lip pale |
| Pain in the left shoulder and the left arm | Nightmare and easily scared | Reddish facial complexion | Stuffy nose | Mouth ulcer |
| Joint and muscle pain | Nightmare | Reddish facial complexion | | Dry mouth |
| Pain in the entire body, sometimes in the upper body, sometimes in the lower body | Palpitation and sleeplessness | Pale facial complexion | | Dry mouth and taste bitter |
| Fever and reduced pain | Irritability and insomnia | Greenish purple facial complexion | | Taste bitter |
| Spinal and lumber pain | Sleeplessness | Redish facial complexion | | Pale lip |
| Hypochondrium pain and distention | Palpitation and insomnia | Reddish facial complexion | | Dry mouth and taste bitter |
| Hypochondrium and abdominal stabbing pain | Nightmare | Yellowish and pale facial complexion | | Dry mouth |
| Continous pain in the neck and the back | Insomnia and forgetful | Grey facial complexion | | Dry mouth and irritable |
| Severe pain in the stomach and left hypochondrium | Lack of sleep | Yellowish and pale facial complexion | | Dry mouth |
| Sever abdominal cramps | | Reddish facial complexion | | Dry mouth |
| Stabbing pain in the hypochrondium | | Pale facial complexion | | |
| Dull pain in the hypochrondium | | Reddish facial complxion | | |
| Lower abdominal distention | | Reddish facial complexion and fever | | |
| Chest distention and abdominal pain | | Pale facial complexion | | |
| Abdominal pain | | Pale facial complexion | | |
| Sudden stomachache | | Pale facial complexion | | |
| Abdominal distention and pain | | Yellowish facial complexion | | |
| Stabbing pain in the abdominal | | Yellowish facial complexion | | |
| Burning pain in the abdominal | | Grey facial complexion | | |
| Burning pain in the abdominal | | Bad grey facial complexion | | |
| Dull, burning pain in the abdominal | | Reddish facial complexion | | |
| Dull pain in the abdominal | | Pale facial complexion | | |
| | | Grey facial complexion and weight loss | | |
| | | Yellowish and pale facial complexion | | |
| | | Yellowish and pale facial complexion, lack of energy | | |
| | | Pale facial complexion | | |

TABLE 1D

| | | 5 symptoms | | |
|---|---|---|---|---|
| Pharynx | Vomit | Spirit | menses | Vaginal discharge |
| Itchy | Vomit and lack of appetite | Fatigue | Irregular menstruation | Emission, virginal discharge |
| Pain | Vomit | Fatigue | Amenorrhea, reduced mentrual flow | |
| Swell | Vomit | Irritable | Amenorrhea | |
| Sore throat | Chest tightness, vomit | Fatigue | | |
| Dry mouth | Nausea | Anxious | | |
| Dry mouth sore throat | Vomit | Irritable | | |
| Sputum in the chest/throat | Nausea | Irritable | | |
| Difficulty in swallowing | Ptyalism | Lack of energy | | |
| Dry throat | Vomit | Palpitation | | |
| Loss of voice | Nausea | Palpitation, restless | | |
| Sore throat | Vomit | Palpitation, restless | | |
| | Ptyalism | Aggressive | | |
| | Vomit | Restless | | |
| | Vomit with sticky, white fluid | Anxious | | |
| | Vomit with reddish fluid | Fatigue | | |
| | Vomit | Anxious | | |
| | Vomit acidic liquid | Fatigue | | |
| | Vomit | Palpitation and short breathing | | |
| | Spit | Lack of spirit | | |
| | Vomit | Irritable | | |
| | | Anxious and palpitation | | |
| | | Palpitation and forgetfulness | | |
| | | Fatigue and lack of appetite | | |
| | | Forgetfulness and emission | | |
| | | Anxious | | |
| | | Fatigue | | |
| | | Fatigue and aversion to cold | | |
| | | Faint | | |
| | | Dizziness and faint | | |
| | | Faint | | |
| | | Faint | | |
| | | Faint | | |
| | | Delirium | | |
| | | Irritable | | |
| | | Anxious | | |
| | | Palpitation | | |
| | | Restlessness | | |
| | | Laying down peacefullly | | |
| | | Anxious | | |
| | | Depression | | |
| | | Sigh | | |
| | | Anxious | | |
| | | Irritable | | |
| | | Anxious | | |
| | | Trance | | |
| | | Sadness | | |
| | | Restless, anxious | | |
| | | Restless | | |
| | | Fatigue | | |
| | | Palpitation, timid | | |
| | | Dizziness, palpitation | | |
| | | Anxious | | |
| | | Fatgue | | |
| | | Lack of emotion | | |
| | | Dementia of | | |

TABLE 1D-continued

5 symptoms

| Pharynx | Vomit | Spirit | menses | Vaginal discharge |
|---|---|---|---|---|
| | | consciousness | | |
| | | Trance | | |
| | | Absent minded, lack of normal | | |
| | | Sadness | | |
| | | Speak wildly to close relatives | | |
| | | Destroy property and hurt people | | |
| | | Fatigue | | |
| | | Agitated and weight loss | | |
| | | Fatigue | | |
| | | Delirium | | |
| | | Palpitation and short breath | | |
| | | Irritable and anxious | | |
| | | Fatigue | | |
| | | Timid | | |
| | | Fatigue, sleepy | | |
| | | Palpitation | | |
| | | Irritable | | |
| | | Fatigue | | |
| | | Fatigue | | |
| | | Fatigue, aversion to cold | | |
| | | Fatigue | | |
| | | Irritable, agitated | | |

TABLE 1E

Symptoms identified based on 10 questions

| Tongue | Tongue surface/fur |
|---|---|
| Thin, white | Thin, white |
| Thin white and dry | Thin white and dry |
| Thin, yellowish, reddish on the edge | Thin, yellowish, reddish on the edge |
| Thin, yellowish and slimy fur | Thin, yellowish and slimy fur |
| Thin, yellow | Slimy, white |
| Cool, dry, thin, white | Thin, yellow |
| Warm, dry, thin, yellow | Cool, dry, thin, white |
| White, slimy | Warm, dry, thin, yellow |
| Thin, yellow, slimy, reddish tongue | Thin, yellow, slimy, reddish tongue |
| Thin, yellow, insufficient fluid | Thin, yellow, insufficient fluid |
| Reddish tongue | White smooth |
| Pale | Pale |
| Pale slimy | Little fur, reddish fur |
| White, slippery | Thin, yellowish fur |
| Reddish tognue | Reddish and dry |
| Teeth scar on the tongue | Little fur |
| Dry mouth | Thin fur |
| Fat Tongue | Yellowish fur |
| Pale slippery or grey slimy | Smooth and purplish |
| Pale tongue, white fur | Little fluid |
| Pale tongue | Thin, yellow fur |
| Dark, purplish tongue or with blood masses | Yellow, slimy fur, reddish |
| Yellow, slimy fur | Yellowish fur, reddish |
| Dark, purplish tongue or with blood masses | Pale tongue, white fur |
| White, slimy fur or white, slippery fur | Pale tongue, smooth fur |
| Slimy fur | Yellowish, slimy fur |
| Dark, purplish tongue or with blood masses | White, slimy or white, smooth fur |
| Pinkish tongue | Slimy fur |
| Green or dark purple tongue | White, slimy fur, weak pulse |
| Dark tongue with blood masses | White fur |
| Mouth ulcer | Slimy fur, floating pulse |
| Pink tip of the tongue | White, slimy fur |
| Pale tongue, weak pulse | Yellowish, dry fur, floating pulse |
| tongue with blood masses | Slimy fur |
| Pale tongue | Reddish tongue, little fur |
| Pink tongue, little fur | Reddish tongue, yellowish, slimy fur, grey |
| | Thick slimy fur, floating pulse |
| Pink tongue, yellow slimy grayish fur | Thin, white fur |
| Purplish tongue or with blood masses | Yellowish fur, floating pusle |
| Pale, fat, purplish tongue | Thin, white fur |
| Reddish tongue | White, Slimy fur |
| Reddish tongue | Thin fur |
| Reddish tongue | Yellowish, slimy fur |
| Pinkish tongue | Little fur |
| White, Slimy fur | Yellowish fur |
| Purplish tongue | White, slimy fur |
| Pale tongue | Yellowish, dry fur |
| Speech difficulty | Thin, yellow fur |
| White slimy fur | White slimy or white smooth fur |
| Tongue atrophy | White fur |
| Purplish tongue | Pale fur |
| Yellowish, slimy fur | Little fur |
| Purple tongue | Dry fur |
| Yellowish, slimy fur | Thine, slimy fur |
| Purplish tongue | Yellowish fur, floating pulse |
| Pale tongue | Thick, slimy fur |
| Pale, fat tongue | White, slimy fur |
| Reddish tip of the tongue | Smooth fur |
| Pinkish tongue | |
| Dark, purplish tongue or with blood masses | |
| Red tongue | |
| Red tongue | |
| Pale, fat tongue | |
| Reddish or purplish tip of the tongue | |
| Smooth tongue surface without fur | |

TABLE 1E-continued

Symptoms identified based on 10 questions

| Tongue | Tongue surface/fur |
|---|---|
| Light purplish tongue | |
| Diarrhea, stool with white mucus and blood masses | |
| Diarrhea, stool with dark blood masses | |
| Diarrhea, stool with white mucus | |
| Diarrhea, stool with white mucus and blood masses | |
| Diarrhea with loose watery stool | |
| Reddish, smooth tongue | |
| Reddish tongue | |
| Pinkish tongue | |
| | White, slimy fur |

We claim:

1. A computer-implemented method for representing an ontological information system for illness based on Chinese Traditional Medicine, the method comprising:

generating, through a computer, ontological information comprising symptoms and associated illnesses in Chinese Traditional Medicine in annotated form, wherein the symptoms are categorized as major, minor, tongue surface and pulse according to Chinese Traditional Medicine;

converting, via a semantic net of the computer, the ontological information into logic representations;

providing a graphic system of queries regarding symptoms for receiving user input into the computer based on the ontological information;

receiving user input symptoms in response to the queries;

parsing illnesses in the ontological information associated with the user input symptoms;

matching the user input symptoms with expected symptoms of parsed illnesses;

assigning a weighted value to a user input symptom matched with an expected symptom of a parsed illness based on the symptom category, wherein if a matched user input symptom is of greater importance to the parsed illness, the matched user input symptom is assigned a higher weighted value, and if a matched user input symptom is of less importance to the parsed illness, the matched user input symptom is assigned a lower weighted value;

calculating a relevance index by comparing the user input symptoms with the expected symptoms of parsed illnesses, each parsed illness that has a user input symptom matching an expected symptom of the respective parsed illness having an entry in the relevance index, each entry in the relevance index comprising a parsed illness and a numerical value being the number of user input symptoms that match the expected symptoms of the respective parsed illness;

calculating a frequency index to evaluate the parsed illness and using the frequency index in calculating a modified relevance index, wherein the frequency index is calculated based on:

determining a total number of user input symptoms that match the expected symptoms of a respective parsed illness;

separating each user input symptom that matches an expected symptom of a respective parsed illness into a sub-category;

assigning a weighted value to each sub-category;

for each respective sub-category of a parsed illness, calculate a quotient by dividing the total number of matched user input symptoms with the number of user input symptoms in the sub-category, then calculate a product by multiplying the quotient by the respective weighted value for the sub-category, and then calculate a sum for each parsed illness by adding together each product for each sub-category of the parsed illness;

providing a graphic index comprising a ranked column of parsed illnesses and an adjacent column comprising a relevance index value for each respective parsed illness, the ranked column of parsed illnesses being in ascending order of a parsed illness having a highest number of user input symptoms matching the expected symptoms of the respective parsed illness to a parsed illness having a lowest number of user input symptoms matching the expected symptoms of the respective parsed illness, the adjacent column providing the number of matched user input symptoms with the expected symptoms of each respective parsed illness;

when the frequency index for the parsed illness falls below a threshold value, and when one or more unmatched user input symptom is in a major symptom category, adding to the ontological information a new disease descriptor having the matched user input symptoms and the one or more unmatched user input symptom in the major symptom category; and communicating to the user, illnesses in Chinese Traditional Medicine derived from the semantic net associated with the user input symptoms, wherein the semantic net is a document object model, and wherein the expected symptom is selected from: chills and fever; sweat; cough; sputum; pain; sleep disturbance; vomiting; vaginal discharge; and alterations in complexion, nose, lips, throat, pharynx or tongue.

2. The method of claim 1, wherein the annotated form of the ontological information is provided in Extensible Markup Language (XML).

3. The method of claim 1, wherein the ontological information is stored in a memory of the computer.

4. The method of claim 1, which is practiced in a network environment.

5. The method of claim 1, wherein the sub-categories comprise at least one of the following: major symptoms, minor symptoms, tongue surface symptoms, and pulse symptoms, wherein different weighted values are assigned to the matched user input symptoms in different categories.

6. The method of claim 1, further comprising evaluating an illness in Chinese Traditional Medicine parsed by the semantic net based on the frequency index of the parsed illness.

7. A computer program product, tangibly embodied in non-transitory computer-readable media, for representing an ontological information system for illness based on Chinese Traditional Medicine, the product comprising instructions to cause a computer to:

generate ontological information regarding symptoms and associated illnesses in Chinese Traditional Medicine in annotated form, wherein the symptoms are categorized as major, minor, tongue surface and pulse according to Chinese Traditional Medicine;

convert, via a semantic net, the ontological information into logic representations;

provide a graphic system of queries regarding symptoms for receiving user input into the computer based on the ontological information;

receive user input symptoms in response to the queries;
parse illnesses in the ontological information associated with the user input symptoms;
match the user input symptoms with expected symptoms of parsed illnesses;
assign a weighted value to a user input symptom matched with an expected symptom of a parsed illness based on the symptom category, wherein if a matched user input symptom is of greater importance to the parsed illness, the matched user input symptom is assigned a higher weighted value, and if a matched user input symptom is of less importance to the parsed illness, the matched user input symptom is assigned a lower weighted value;
calculating a relevance index by comparing the user input symptoms with the expected symptoms of parsed illnesses,
each parsed illness that has a user input symptom matching an expected symptom of the respective parsed illness having an entry in the relevance index;
each entry in the relevance index comprising a parsed illness and a numerical value being the number of user input symptoms that match the expected symptoms of the respective parsed illness;
calculate a frequency index to evaluate the parsed illness and using the frequency index in calculating a modified relevance index, wherein the frequency index is calculated by:
determining a total number of user input symptoms that match the expected symptoms of a respective parsed illness;
separating each user input symptom that matches an expected symptom of a respective parsed illness into a sub-category;
assigning a weighted value to each sub-category;
for each respective sub-category of a parsed illness, calculate a quotient by dividing the total number of matched user input symptoms with the number of user input symptoms in the sub-category, then calculate a product by multiplying the quotient by the respective weighted value for the sub-category, and then calculate a sum for each parsed illness by adding together each product for each sub-category of the parsed illness;

provide a graphic index comprising a ranked column of parsed illnesses and an adjacent column comprising a relevance index value for each respective parsed illness;
the ranked column of parsed illnesses being in ascending order of a parsed illness having a highest number of user input symptoms matching the expected symptoms of the respective parsed illness to a parsed illness having a lowest number of user input symptoms matching the expected symptoms of the respective parsed illness;
the adjacent column providing the number of matched user input symptoms with expected symptoms of each respective parsed illness;
determine, when the frequency index for the parsed illness falls below a threshold value, whether one or more unmatched user input symptom is in a major symptom category;
in response to determining that the one or more unmatched user input symptom is in the major symptom category, add to the ontological information a new disease descriptor having the matched user input symptoms and the one or more unmatched user input symptom in the major symptom category; and
communicate to the user, illnesses in Chinese Traditional Medicine derived from the semantic net associated with the user input symptoms,
wherein the semantic net is a document object model, and
wherein the expected symptom is selected from: chills and fever; sweat; cough; sputum; pain; sleep disturbance; vomiting; vaginal discharge; and alterations in complexion, nose, lips, throat, pharynx or tongue.

8. The product of claim 7, wherein the annotated form of the ontological information is provided in Extensible Markup Language (XML).

9. The product of claim 7, wherein the sub-categories comprise at least one of the following: major symptoms, minor symptoms, tongue surface symptoms, and pulse symptoms, wherein different weighted values are assigned to the matched user input symptoms in different categories.

10. The product of claim 7, further comprising instructions to cause the computer to evaluate an illness in Chinese Traditional Medicine parsed by the semantic net based on the frequency index of the parsed illness.

* * * * *

UNITED STATES PATENT AND TRADEMARK OFFICE
CERTIFICATE OF CORRECTION

PATENT NO. : 10,089,391 B2
APPLICATION NO. : 13/318849
DATED : October 2, 2018
INVENTOR(S) : Wilfred Wan Kei Lin et al.

It is certified that error appears in the above-identified patent and that said Letters Patent is hereby corrected as shown below:

In the Specification

Column 5:
Line 63, "surface or tongue" should read -- surface of tongue --.

Column 6:
Line 8, "GUT" should read -- GUI --.
Line 57, "data. Grid." should read -- data Grid. --.

Column 7:
Line 43, "betreated" should read -- be treated --.

Column 11:
Line 8, "Lumber pain" should read -- Lumbar pain --.
Line 42, "lumber aching" should read -- lumbar aching --.

Column 13:
Line 23, "headahce" should read -- headache --.
Line 56, "Fatigue in th" should read -- Fatigue in the --.

Column 21:
Line 39, "Sever abdominal" should read -- Severe abdominal --.

Column 23:
Line 15, "sore throut" should read -- sore throat --.

Column 26:
Line 56, "Thine, slimy fur" should read -- Thin, slimy fur --.

Signed and Sealed this
Eighteenth Day of June, 2019

Andrei Iancu
*Director of the United States Patent and Trademark Office*